US006270465B1

(12) United States Patent
Keith et al.

(10) Patent No.: US 6,270,465 B1
(45) Date of Patent: Aug. 7, 2001

(54) METHOD AND APPARATUS FOR CATHETER EXCHANGE BY GUIDE WIRE-CAPTIVATION

(75) Inventors: Peter T. Keith, Edina; Daniel O. Adams, Blaine, both of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 07/830,479

(22) Filed: Feb. 4, 1992

Related U.S. Application Data

(63) Continuation of application No. 07/398,756, filed on Aug. 25, 1989, now abandoned.

(51) Int. Cl.[7] .................................................. A61M 29/02
(52) U.S. Cl. ........................ 600/585; 604/103.04; 606/194
(58) Field of Search ................................. 604/53, 96–103, 604/165, 169, 170, 280, 510, 101.01–101.05, 103.04, 164.13; 606/194; 128/657, 658, 772; 600/585

(56) References Cited

U.S. PATENT DOCUMENTS

| | | | |
|---|---|---|---|
| 2,919,697 | * | 1/1960 | Kim ........................................ 604/102 |
| 4,166,468 | * | 9/1979 | Haynie ................................... 604/256 |
| 4,285,341 | * | 8/1981 | Pollack ................................... 604/101 |
| 4,445,892 | * | 5/1984 | Hussein et al. ............................ 606/7 |
| 4,606,347 | * | 8/1986 | Fogarty et al. ........................ 604/102 |
| 4,730,616 | | 3/1988 | Frisbie et al. . |
| 4,771,777 | * | 9/1988 | Horzewski et al. ................... 606/194 |
| 4,798,193 | | 1/1989 | Giesy et al. . |
| 4,820,349 | * | 4/1989 | Saab ..................................... 606/194 |
| 4,827,941 | * | 5/1989 | Taylor et al. ......................... 128/657 |
| 4,832,028 | * | 5/1989 | Patel .................................... 606/194 |
| 4,844,092 | * | 7/1989 | Rydell et al. ......................... 128/772 |
| 4,846,174 | * | 7/1989 | Willard et al. ....................... 606/194 |
| 4,881,547 | * | 11/1989 | Danforth .............................. 606/194 |
| 4,917,102 | * | 4/1990 | Miller et al. ......................... 128/657 |
| 4,932,959 | * | 6/1990 | Horzewski et al. ..................... 604/96 |
| 4,944,740 | * | 7/1990 | Buchbinder et al. ................. 606/194 |

FOREIGN PATENT DOCUMENTS

| | | |
|---|---|---|
| 0416 734 A1 | 7/1990 | (EP) . |
| 380 227 | 8/1990 | (EP) . |

* cited by examiner

*Primary Examiner*—Ralph A. Lewis
(74) *Attorney, Agent, or Firm*—Crompton, Seager & Tufte, LLC

(57) ABSTRACT

An apparatus for exchanging over-the-wire balloon catheters engages a guide wire within a guide catheter. In one embodiment the engagement is by an inflatable balloon in the guide catheter. Alternatively, the engagement is accomplished by a captivation wire in the guide catheter that has a collapsible loop portion through which the guide wire extends. Inflation of the balloon or closing the loop portion of the captivation wire within the guide catheter traps the guide wire and restricts its movement relative to the guide catheter. Once the guide wire position is fixed, withdrawal of a first balloon catheter and subsequent introduction of a second balloon catheter over the guide wire is possible without moving the guide wire longitudinally. Thus, the positioning of the guide wire over a stenosis to be dilated is not disturbed.

20 Claims, 5 Drawing Sheets

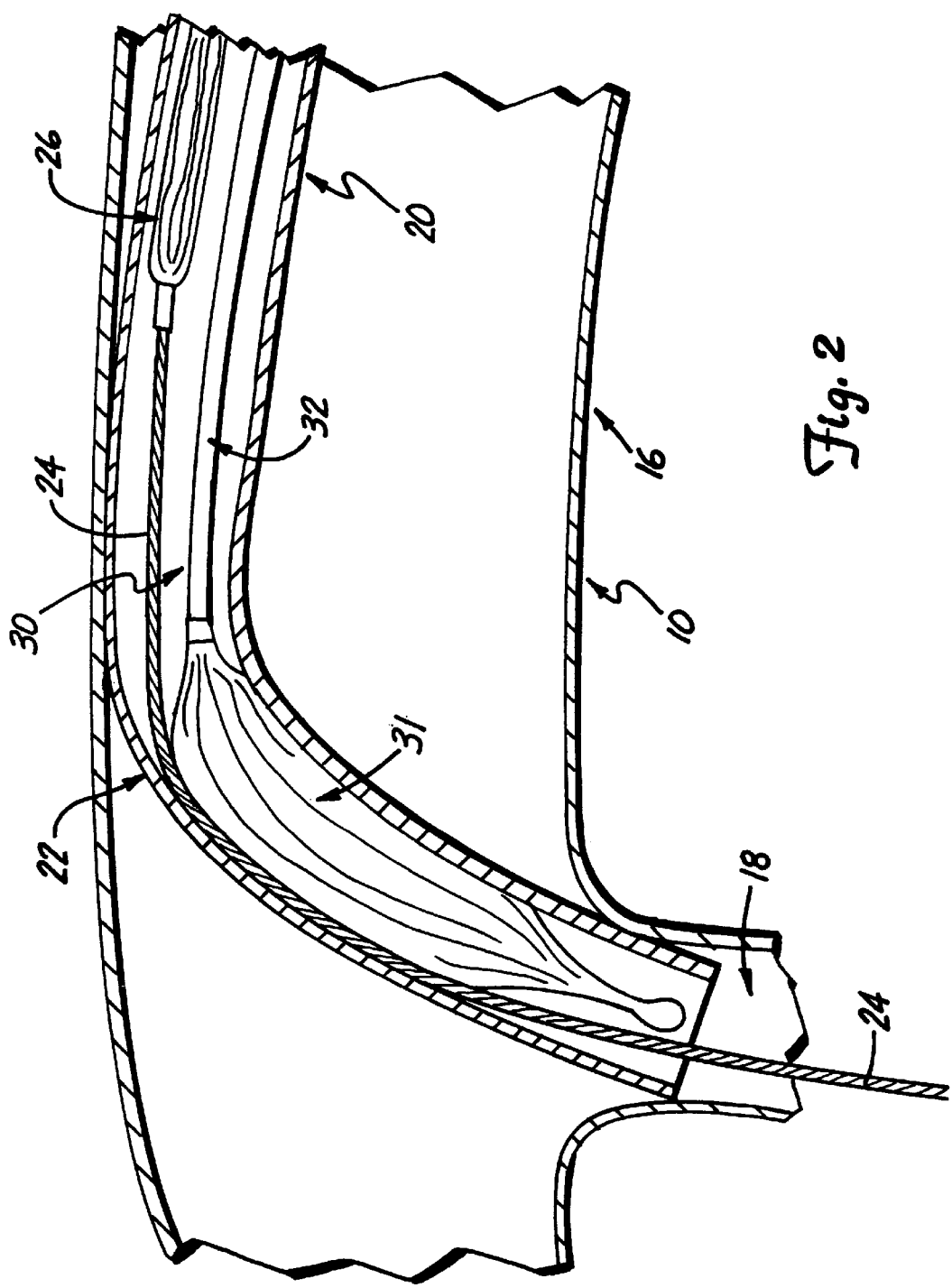

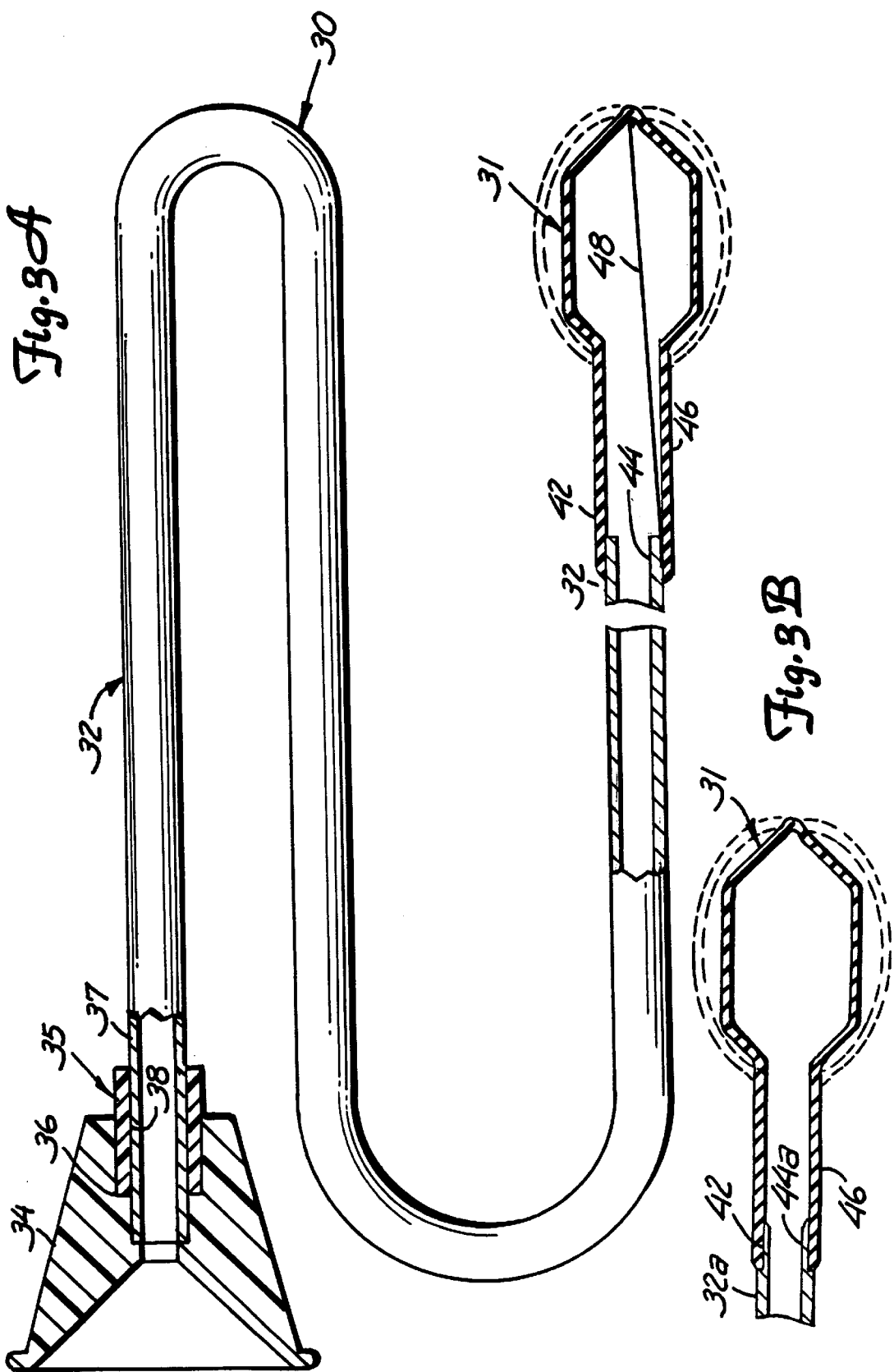

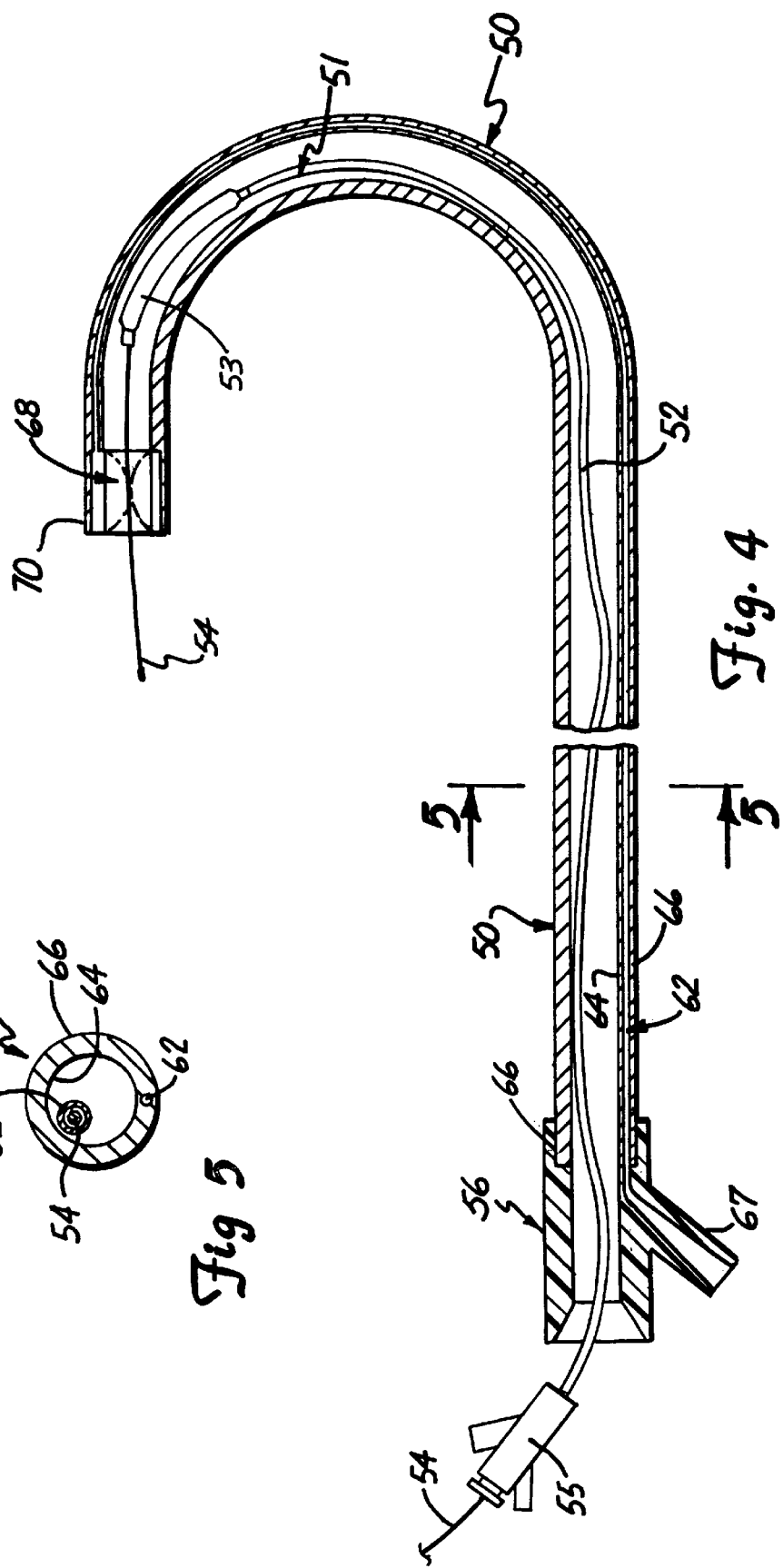

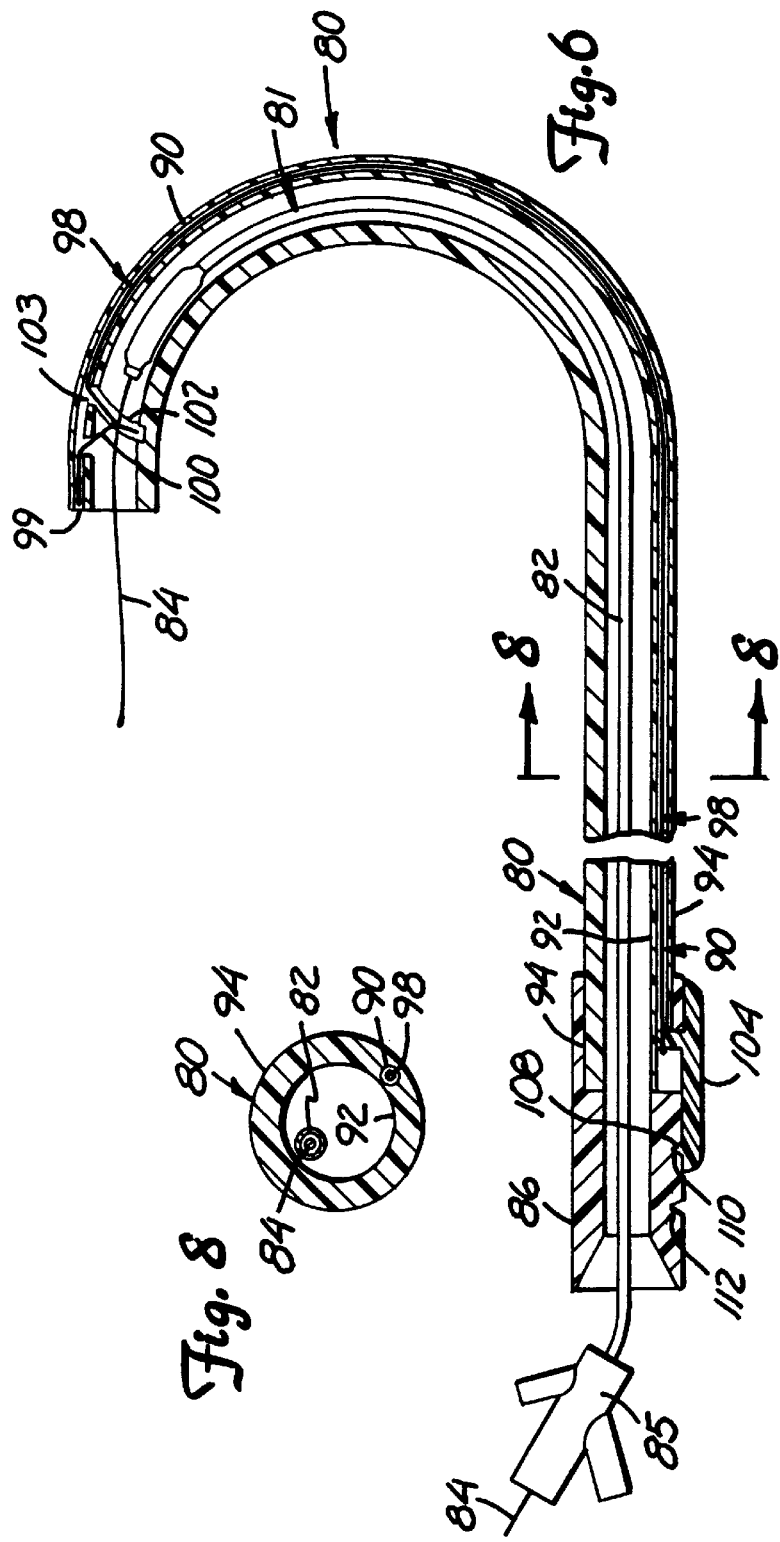

METHOD AND APPARATUS FOR CATHETER EXCHANGE BY GUIDE WIRE-CAPTIVATION

This is a continuation of application Ser. No. 07/398,756, filed on Aug. 25, 1989, abandoned as of the date of this application.

BACKGROUND OF THE INVENTION

1. Field of the Invention

The present invention relates to the field of angioplasty. In particular, the present invention relates to an apparatus and method for facilitating the exchange of a dilatation balloon catheter on a guide wire.

2. Description of the Prior Art

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to re-establish acceptable blood flow through the artery.

Two types of dilatation catheters are "over-the-wire" catheters and "non-over-the-wire" catheters. An over-the-wire catheter is one in which a separate guide wire lumen (sometimes called a "thru lumen") is provided so that a guide wire can be used to establish a path through the stenosis. The dilatation catheter is then advanced over the guide wire until the balloon is positioned across the stenosis. One problem with the over-the-wire catheter is the inability to maintain the position of the guide wire within the vascular system when removing the catheter, and when exchanging it for one of a smaller (or larger) balloon diameter.

It is desirable to maintain the position of the guide wire across the stenosis during the exchange of catheters to ensure the safety and speed of the angioplasty procedure. Attempts to alleviate the problem of guide wire movement include the use of long or "exchangeable" guide wires, or extendable guide wires. These guide wires are of a length such that a proximal portion of the guide wire extends outside the patient's body while a distal portion of the guide wire passes through the body and across the stenosis. Thus, during an exchange of balloon catheters on the wire, the guide wire position across the stenosis is maintained by holding onto a proximal segment of the guide wire from outside of the body. However, guide wire movement relative to the stenosis still occurs despite such external fixation of the guide wire. These guide wires also have the disadvantage of being cumbersome and difficult to handle while maintaining the guide wire position across the stenosis. For example, a length of guide wire of approximately 150 cm must be maintained outside the body (either by an extension or by a 300 cm long base guide wire). Furthermore, x-ray fluoroscopy must be used during the exchange in order for the operator to see the wire being held in position across the stenosis. This use of fluoroscopy results in an undesirable, excessive exposure of x-ray radiation to the patient and also to the attendant medical personnel.

A non-over-the-wire catheter (also called a "fixed wire" catheter) acts as its own guide wire, so that the exchange of catheters necessarily requires removal of the catheter/guide wire assembly from the stenosis area. Thus, when accomplishing an exchange with the "non-over-the-wire" catheter, the path to the stenosis must be re-established when replacing the catheter with one having a different balloon diameter.

In both types of catheter/guide wire systems, it is difficult to effectively maintain or realign the guide wire across the stenosis. In addition, the exchange often requires more than one person to perform the procedure and requires extensive use of fluoroscopy resulting in excessive x-ray exposure to the patient.

SUMMARY OF THE INVENTION

Unlike previous catheter exchange systems which allow guide wire movement during an exchange at the distal end of the guide catheter and near the stenosis, the present invention has the advantage of fixing the guide wire position directly at the distal end of guide catheter and near the stenosis, thereby preventing guide wire movement relative to the stenosis.

The present invention is an improved apparatus for use in exchanging an over-the-wire balloon catheter on a guide wire, with the guide wire running through a guide catheter. The improved apparatus is a means for selectively engaging the guide wire within the guide catheter to restrict longitudinal movement of the guide wire relative to the guide catheter. The means for selectively engaging further include a means for urging a portion of the guide wire against an inner portion of the guide catheter.

In some preferred embodiments of the present invention, an inflation lumen extends longitudinally within the guide catheter. The inflation lumen has a proximal end and a distal end, with the distal end of the inflation lumen being within and adjacent to a distal end of the guide catheter. An inflatable balloon is in fluid communication with the distal end of the inflation lumen, and the inflatable balloon is of a size such that inflation of the balloon within the guide catheter restricts longitudinal movement of the guide wire relative to the guide catheter.

In one preferred embodiment, the inflation lumen is integral with a wall of the guide catheter and in fluid communication with an inflatable balloon that is fixed to a wall of the guide catheter. The inflation lumen provides a fluid path between the proximal end of the guide catheter and the inflatable balloon, wherein the balloon is inflated when pressure is applied to the fluid through the lumen. Upon inflation of the balloon, the guide wire is trapped between the balloon and the inner portion of the guide catheter, and longitudinal guide wire movement with respect to the guide catheter is limited.

In another preferred embodiment, the inflation lumen and an inflatable balloon both are separate from the guide catheter, and are thus movable longitudinally within the guide catheter. The inflation lumen provides a fluid path between the proximal end of the guide catheter and the inflatable balloon, wherein the balloon is inflated when pressure is applied to the fluid through the lumen. Upon inflation of the balloon, the guide wire is captured between the balloon and the guide catheter, and longitudinal guide wire movement with respect to the guide catheter is limited.

In another preferred embodiment of the present invention, a captivation wire extends longitudinally within the guide catheter. The captivation wire has a distal end, a loop portion, and a proximal end. The distal end of the captivation wire is secured to the guide catheter, and the loop portion of the captivation wire is within and just proximal to the distal end of the guide catheter. The loop portion has an open loop state, whereby unrestricted longitudinal movement of the guide wire through the loop portion and relative to the guide catheter is permitted. The loop portion also has a closed loop state, whereby longitudinal movement of the guide wire relative to the guide catheter is limited.

In one embodiment, the captivation wire extends longitudinally through and is slidably received in a lumen formed in a wall of the guide catheter. A spiraled recess is formed within an inner wall of the guide catheter to receive the loop portion of the captivation wire when in its open loop state. A tab member is connected to the proximal end of the captivation wire and is mounted to the proximal end of the guide catheter. The tab member is movable longitudinally with respect to the guide catheter between a first distal position and a second proximal position. When the tab member is in its first distal position, the captivation wire is in the open loop state and when the tab member is in its second proximal position, the captivation wire is in the closed loop state. The tab member also includes detent means to selectively retain the tab member in the first distal position or the second proximal position.

The unique and inventive method for limiting a guide wire in a guide catheter from longitudinal movement with respect to the guide catheter involves two simple steps: (1) providing a means for selectively engaging the guide wire within the guide catheter, and (2) manipulating the means for engaging to force the guide wire against an inner portion of the guide catheter, thereby fixing the guide wire position with respect to the guide catheter. Preferably, the means for engaging the guide wire is positioned within the guide catheter adjacent a distal end of the guide catheter. The guide wire position is thus fixed at a location somewhat close to the stenosis, as opposed to trying to hold the guide wire in position by grasping the guide wire adjacent its proximal end, at a location outside of the body and very remote from the stenosis.

In one embodiment of the inventive method, the means for engaging the guide wire is an inflatable wire-captivation balloon. The wire-captivation balloon is provided within the guide catheter and inflated to a size such that the balloon forces the guide wire against an inner portion of the guide catheter, thereby fixing the guide wire position with respect to the guide catheter.

To exchange a first over-the-wire catheter on a guide wire in a patient's vascular system for a second over-the-wire catheter on the guide wire, this inventive exchange method includes a first step of providing the inflatable wire-captivation balloon within the guide catheter. Next, a proximal end of the guide wire is held outside the vascular system to maintain position of the guide wire longitudinally relative to the guide catheter, while the balloon of the first over-the-wire catheter is moved on the guide wire into the guide catheter to a position that is proximal of the wire-captivation balloon. The wire-captivation balloon is then inflated to maintain the position of the guide wire relative to longitudinal movement with respect to the guide catheter. Once the guide wire position is fixed within the guide catheter, the proximal end of the guide wire is released. Then, the first over-the-wire catheter is withdrawn from a proximal end of the guide wire, and a second over-the-wire catheter is installed onto the proximal end of the guide wire. The balloon of the second over-the-wire-catheter is moved to a position just proximal of the wire-captivation balloon, and then the proximal end of the guide wire is again held outside of the vascular system to maintain position of the guide wire longitudinally relative to the guide catheter and vascular system. Next, the wire-captivation balloon is deflated to release the guide wire from its fixed position relative to the guide catheter, and finally the second over-the-wire catheter is moved distally of the wire-captivation balloon and across the lesion for further dilatation.

In another embodiment of the inventive method, the means for engaging the guide wire is a wire-captivation wire. The wire-captivation wire is provided within the guide catheter and when a loop portion of the wire-captivation wire is closed, the guide wire is forced against an inner portion of the guide catheter, thereby fixing the guide wire position relative to the guide catheter.

An exchange of over-the-wire catheters by the inventive method using the wire-captivation wire requires a wire-captivation wire within the guide catheter that has a looped portion through which the guide wire extends. In use, the looped portion closes to trap the guide wire against an inner portion of the guide catheter and opens to release the guide wire. The wire-captivation wire replaces the wire-captivation balloon of the previous exchange method and in particular, the looped portion of the wire-captivation wire effectively replaces the inflatable wire-captivation balloon. All the steps of the previous exchange method are duplicated except for the following: (1) instead of inflating the balloon to a size such that movement of the guide wire longitudinally relative to the guide catheter is limited, the looped portion of the captivation wire is closed to a size such that movement of the guide wire longitudinally relative to the guide catheter is limited, and (2) instead of deflating the inflatable balloon to release the guide wire from its fixed position relative to the guide catheter, the looped portion is opened to release the guide wire.

BRIEF DESCRIPTION OF THE DRAWINGS

FIG. 2 is an enlarged fragmentary sectional view of a portion of FIG. 1 which shows guide wire captivation.

FIG. 3A is an enlarged elevational view showing one preferred embodiment of an inflation lumen and an inflatable captivation balloon, with some parts shown in section.

FIG. 3B is an enlarged fragmentary sectional view of another preferred embodiment of the inflatable captivation balloon.

FIG. 4 is a sectional view of another preferred embodiment of the present invention, showing an inflation lumen and an inflatable balloon, in combination with a guide catheter.

FIG. 5 is a sectional view as taken on line 5—5 in FIG. 4.

FIG. 6 is a sectional view of another preferred embodiment of the present invention, showing a captivation wire in combination with a guide catheter.

FIG. 7 is an enlarged fragmentary sectional view of a portion of FIG. 6 which shows guide wire captivation.

FIG. 8 is a sectional view as taken on line 8—8 in FIG. 6.

DETAILED DESCRIPTION OF THE PREFERRED EMBODIMENTS

Basic Angioplasty Components and Procedure

Figure 1:
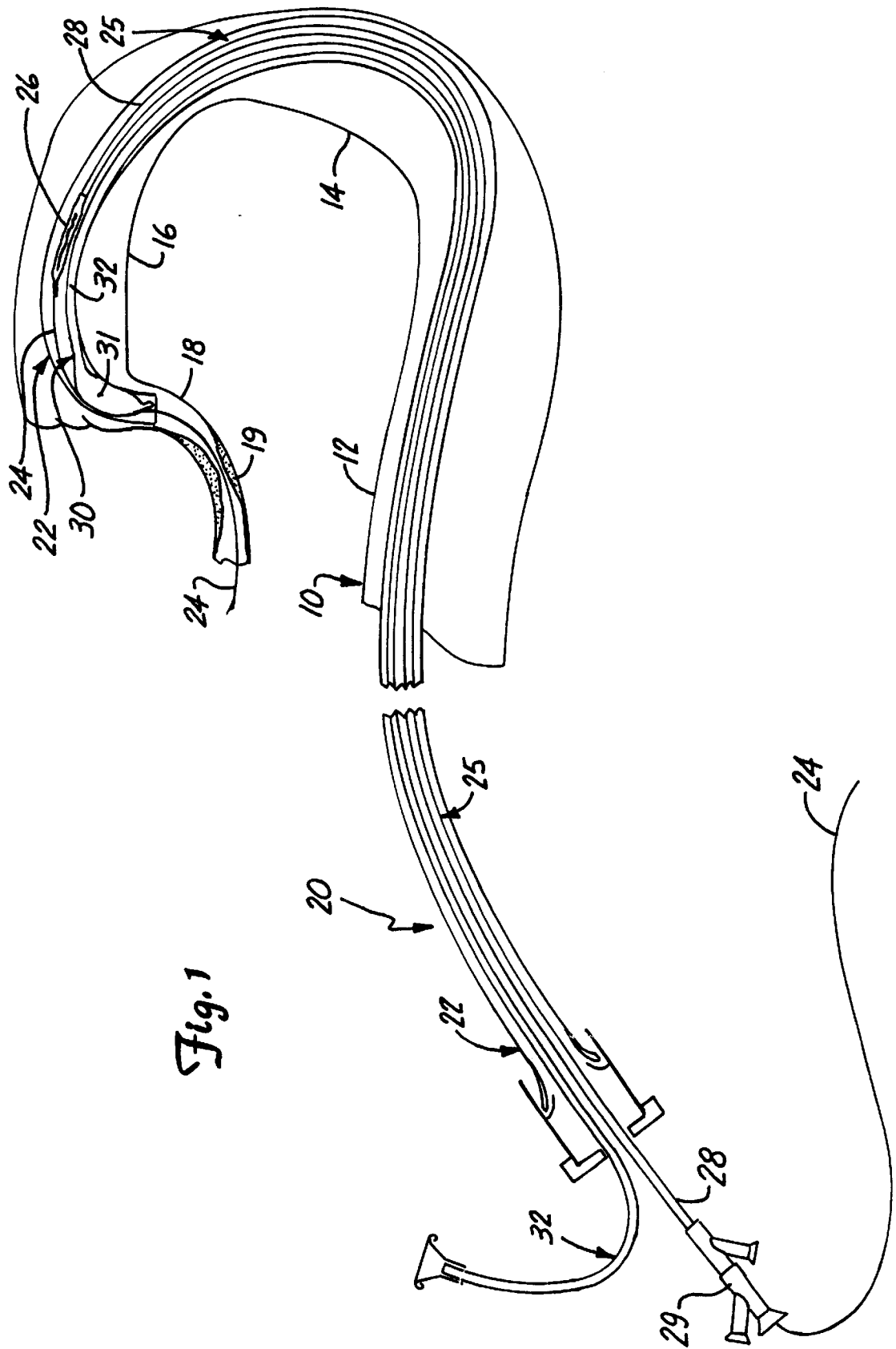
FIG. 1 is a diagrammatic view of an angioplasty balloon catheter system incorporating the present wire-captivation invention.

A vascular system 10 and a balloon catheter system 20 are shown in FIG. 1 and shown in FIG. 2 in fragmentary detail.

In an angioplasty procedure, entry into the vascular system is typically through the femoral artery in the thigh. The proximal portion of the vascular system 10 is not shown, but will be described for anatomical reference. Continuing up from the femoral artery is an iliac artery and, then an abdominal aorta, which extends into a thoracic aorta. The distal portion of the vascular system 10 as shown in FIG. 1 begins just distal of the thoracic aorta (not shown) and extends into a descending aorta 12, an arch of aorta 14, and an ascending aorta 16. Extending from the ascending aorta 16 is a coronary artery 18, in which a stenosis 19 is formed. The stenosis 19 is a formation of plaque within the coronary artery 18 which restricts blood flow.

The balloon catheter system 20 includes a guide catheter 22, a guide wire 24 extending through the guide catheter 22, and a dilatation catheter 25 with a distal balloon 26 mounted on a balloon catheter main shaft 28. The dilatation catheter 25 is an over-the-wire catheter, with its main shaft 28 extending over the guide wire 24. A proximal end of the main shaft 28 is connected to an inflation manifold 29, out of which a proximal portion of the guide wire 24 protrudes.

The basic angioplasty procedure consists of inserting the guide catheter 22 into the vascular system 10 at the femoral artery (not shown). The guide catheter 22 is pushed up through the previously described (and not shown) proximal portion of the vascular system 10 until the descending aorta 12 is reached. Thereafter, the guide catheter 22 is further pushed through the arch of aorta 14, the ascending aorta 16, and up to the mouth of the coronary artery 18, where the stiffness of the guide catheter 22 is such that the guide catheter 22 cannot be extended through the tortuous lumens of the artery tree to the stenosis 19.

Next, the distal end of dilatation catheter 25 is loaded onto and over the proximal end of guide wire 24 and pushed up the guide wire 24 until a distal end of dilatation catheter 25 is adjacent to a distal end of the guide wire 24. Then, the assembled combination of guide wire 24 and dilatation catheter 25 are inserted into and pushed up through the proximal end of guide catheter 22, retracing the already established path of the guide catheter 22 through the patient's vascular system 10. The guide wire 24 and dilatation catheter 25 are pushed until they both extend out of a distal end of the guide catheter 22. The tip of the guide wire 24 with the loaded dilatation catheter 25 is then manipulated into the artery tree to the stenosed artery and then finally, across the stenosis 19.

The stenosis 19 as shown in FIG. 1 is adjacent the ostium of the coronary artery 18. Frequently, the stenosis 19 is farther from the ostium of the coronary artery 18 and is found in an arterial branch extending from the coronary artery 18. The route from the coronary artery to the stenosis/arterial branch is often a tortuous path of turns and twists through several blood vessels in an arterial tree. In such a case, the guide catheter 22 is too stiff to be guided down the tortuous path, so the guide wire 24 and the dilatation catheter 25 must extend some distance beyond the distal end of the guide catheter 22 down the tortuous arterial path in order to reach the stenosis 19.

Dilatation Catheter Exchange—Prior Art Techniques

The profile of the deflated balloon 26 of a dilatation catheter 25 is sometimes too large to fit through the stenosis 19, or the balloon diameter is so small that upon inflation of the balloon 26, the stenosis 19 is not sufficiently dilatated. When this difficulty occurs, the balloon 26 must be exchanged for one of a different size (smaller or larger), so that the stenosis 19 can be crossed and properly treated upon inflation of the balloon 26. The dilatation catheter 25 may also have poor control or low flexibility resulting in an inability to track to the stenosis 19. In this case, the dilatation catheter 25 must be exchanged for one with better tracking characteristics so that the stenosis 19 may be reached and crossed.

A balloon catheter exchange with an extended or extendable guide wire begins by a physician holding onto the extended guide wire 24 extending outside the body at the femoral artery (to fix the position of the guide wire across the stenosis). Then, a second physician withdraws the dilatation catheter 25 proximally from the stenosis 19 and back through the tortuous path of arterial branches to the distal end of the guide catheter 22. The second physician must incrementally remove the dilatation catheter 25 proximally over the guide wire 24 while the first physician grasps an exposed proximal portion of the guide wire 24. As the dilatation catheter 25 is moved proximally, the first physician must continually change the grasping location of the wire 24 to a position proximal of the proximal end of the dilatation catheter 25 in order to maintain the position of the guide wire 24 relative to the stenosis 19. This is necessary since the removal of the catheter 25 by the second physician urges the guide wire 24 proximally back out of the vascular system. Therefore, the first physician must continually urge or "advance"the guide wire 24 distally into the catheter 25 at the same time and in equal length movements that the second physician is withdrawing the catheter 25 proximally from the wire 24 and vascular system 10.

It is desirable to hold the guide wire 24 in place across the stenosis 19 during withdrawal of dilatation catheter 25 to eliminate the need to re-establish the position of the guide wire 24 down the tortuous path and across the stenosis 19 after the catheter on the wire is exchanged. More importantly, being able to hold the guide wire 24 in place prevents excess movement of the distal end of the guide wire 24, which can result in the guide wire 24 damaging the heart.

To complete the exchange process, the dilatation catheter 25 is further withdrawn proximally through the vascular system 10 in the path established by the guide catheter 22 until the dilatation catheter 25 is removed from the body at the femoral artery. Upon removal of the dilatation catheter 25 from the femoral artery, a portion of the guide wire 24 is exposed between the proximal end of the guide catheter and the distal end of the dilatation catheter 25. The first physician grasps the guide wire 24 at this exposed portion to hold the guide wire 24 in position across the stenosis 19 while the dilatation catheter 25 is continually withdrawn proximally relative to the guide wire until it is completely removed from the proximal end of the guide wire.

A second dilatation catheter is then placed on the proximal end of the guide wire 24 and moved distally over the guide wire 24 up through the guide catheter 22 and down the tortuous path of arterial branches until the balloon of the second dilatation catheter is pushed across the stenosis 19. As required during withdrawal of the original dilatation catheter 25, the guide wire 24 must be held in position across the stenosis 19 at all times during the insertion of the second dilatation catheter. Again, this prevents the guide wire 24 from moving distally so as to damage the heart, as well as avoiding the difficulty of re-establishing a path to and across the stenosis 19.

During the exchange of dilatation catheters as described, the guide wire 24 must continually and skillfully be manipulated from outside the body to maintain its position across the stenosis 19. Note that the reference point to fix the position of the guide wire 24 is outside of the body (the thigh) at a location far removed from the area of the stenosis 19 (the chest). This remote point of control for the guide wire 24 makes the exchange of dilatation catheters very difficult, necessitating the use of two persons to perform the exchange.

The longitudinal position of the guide wire 24 relative to the stenosis 19 must be maintained while simultaneously moving the dilatation catheters over the guide wire 24 longitudinally. To do so, the guide wire 24 must be held in position from outside the body by the first physician while the second physician removes the dilatation catheter 25 from the guide wire 24. This is further complicated by the necessary length (perhaps 150 cm) of the guide wire 24 to facilitate such an exchange which extends outside of the body and is difficult to control during the removal or insertion of a dilatation catheter. Not only is this extra guide wire length quite flexible, but it must be kept sterile, on the table and off the floor.

Furthermore, x-ray fluoroscopy must be used during the exchange for the first physician to know that the guide wire 24 is being held in place across the stenosis 19. The x-ray exposure effectively illuminates the image of a radiopaque tip of the guide wire 24 so that its position within the coronary artery may be observed. This prolonged, continuous x-ray exposure to the patient and the physician/and medical team during the exchange is undesirable due to the limited capability of humans to withstand x-ray radiation. However, without x-ray fluoroscopy this vital exchange procedure would not be possible.

The Present Invention

First Embodiment (FIGS. 1–3)

The present invention, as shown in FIGS. 1–3, employs a guide wire captivation catheter 30 which has an inflatable balloon 31 mounted on a distal end of an elongated flexible shaft 32. The shaft 32 is formed from a flexible hollow tube to provide an inflation fluid path between the inflatable balloon 31 and a proximal end of the shaft 32, which is connected to a suitable inflation device (not shown).

As seen in FIGS. 1 and 2, guide wire captivation catheter 30 is inserted into the guide catheter 22 and its balloon 31 (in an uninflated state) is advanced distally to a position adjacent the distal end of the guide catheter 22. The dilatation catheter 25 is moved proximally on the guide wire 24 (which is held in place by hand) until its balloon 26 (also uninflated) is positioned proximally of the balloon 31. Radiopaque markers on the balloons or their respective shafts permit relative positioning of these components. The guide wire 24 is thus exposed and uncovered distally of the balloon 26 and adjacent the balloon 31 within the distal end of the guide catheter. Inflation of the balloon 31 (as seen in FIGS. 2 and 3) therefore limits longitudinal movement of the guide wire 24 relative to the guide catheter 22. The balloon 31 is of size such that the pressure exerted by its inflation pushes the guide wire 24 against an inner wall of the guide catheter 22. The guide wire 24 is thus captivated or trapped at the distal end of the guide catheter 22, which is near the stenosis 19. This is in contrast to the guide wire "captivation" systems described above (i.e., grasp the guide wire at a point outside the body), where the area of guide wire captivation (grasping) is far removed from the stenosis 19. As such, a distinct advantage of the present invention for guide wire captivation over prior arrangements is more direct and local control over the position of the guide wire 24 at its distal end.

A preferred embodiment for the guide wire captivation catheter 30 of the present invention is shown in FIG. 3A. An inflation manifold 34 is bonded to a strain relief member 35 at a strain relief bond surface 36 and bonded to proximal end 37 of the shaft 32 at another bond surface 38. The inflation manifold 34 is connected to an inflation device (not shown) to provide positive fluid pressure to the inflation lumen in the shaft 32 for inflatable balloon 31 inflation, and negative fluid pressure for balloon 31 deflation. The shaft 32 extends from the inflation manifold 34 to a lumen/balloon joint 42, where a distal end 44 of the shaft 32 is connected to a proximal portion 46 of the balloon 31.

FIG. 3B shows an alternative structure of the distal end of the captivation catheter 30. The structures vary due to the differing types of material used to construct the main shaft 32. As shown in FIG. 3A, when the main shaft 32 is made of a flexible stainless steel material, the distal end 44 of shaft 32 has a support wire 48 secured thereto to extending within the balloon 31 from its proximal end to its distal end. The support wire 48 adds rigidity to the balloon 31, so that upon insertion and movement of the balloon 31 within the guide catheter 22, the balloon will not fold back on itself, and is capable of being forced through a tight area.

As shown in FIG. 3B, when the main shaft 32a is made of a plastic polyethylene material, the distal end 44a of shaft 32a is necked down in order to receive the proximal portion 46 of balloon 31. This arrangement creates a more stable bonding structure for balloon 31 when the main shaft 32a is a plastic material. In either case, the distal end of the shaft may optionally be extended in a necked fashion to the distal end of balloon to provide additional structural support to the balloon. The extended necked shafts would thus include inflation paths therethrough to allow the inflation fluid to fill the balloon chamber since the shaft would extend through the entire length of the balloon.

The inflation balloon 31, in its deflated state, preferably has a profile under 0.030 inches in diameter, with a length of approximately 2.5 cm. The inflatable balloon 31 is preferably a polymer material such as a polyolefin. Upon inflation of the balloon 31, its maximum outer diameter is preferably 0.090 inches or just larger than the guide catheter 22 in which it is being utilized. In FIGS. 3A and 3B, the balloon is shown inflated in phantom.

The shaft 32 is preferably formed from an elongated flexible thin-walled tube, preferably of stainless steel, polyethylene or polyamide with a low friction coating on its outer surface such as Teflon or silicone. The shaft 32 preferably has a 0.014 inch inner diameter and a 0.019 inch outer diameter, with a total length of approximately 100 cm. The tube defining shaft 32 preferably has a wall thickness of 0.0025 inch.

The inflation fluid is preferably a saline solution or a solution consisting of fifty percent saline and fifty percent contrast media, where the contrast media may be remagrafin 76. The fifty percent contrast media solution is used when it is desirable to view the balloon expansion using fluoroscopy.

Incorporating this preferred embodiment of the present invention, the basic angioplasty procedure as previously described is followed until it becomes necessary to effect a dilatation catheter exchange on the guide wire.

The inventive method of balloon catheter exchange begins by inserting the guide wire captivation catheter 30 into the guide catheter 22 at the femoral artery (not shown)

and moving it distally until the balloon 31 is adjacent and just proximal to the distal end of the guide catheter 22. Next, a proximal end of the guide wire 24 is held outside of the vascular system 10 to maintain the position of the guide wire 24 longitudinally relative to the guide catheter 22 and vascular system 10. The dilatation catheter 25 is then withdrawn proximally from the stenosis 19 and coronary arteries until its balloon 26 is within the distal end of the guide catheter 22 and proximal to the balloon 31. The balloon 31 is manually positioned by manipulating that portion of the shaft 32 outside the body. Once the balloon 31 is positioned, it is then inflated as seen in FIG. 2. The balloon 31 inflates to a diameter which fills the guide catheter 22 inner diameter and pushes the guide wire 24 against an inner wall of the guide catheter 22, thereby limiting longitudinal movement of the guide wire 24 relative to the guide catheter 22 and relative to the stenosis 19 (assuming the guide catheter 22 is not moved within the vascular system). Inflation of the balloon 31 is accomplished by introducing a fluid under pressure into the inflation manifold 34, through the inflation lumen of the shaft 32, and into the balloon 31.

After the guide wire 24 position is fixed by inflation of the balloon 31, the proximal end of the guide wire is released and the dilatation catheter 25 is moved proximally over the guide wire 24, out of the body and removed off of the proximal end of the guide wire 24. Likewise, a second dilatation catheter is placed on the proximal end of the guide wire 24 and moved distally over the guide wire 24 through the guide catheter 22 to a point just proximal of the balloon 31. The balloon 31 is then deflated, thereby freeing the guide wire 24 from its captive or fixed-position state. The second dilatation catheter is then further moved distally along the guide wire 24 past the distal end of the guide catheter 22 and through the arterial branches up to the stenosis 19. This occurs while the proximal end of the guide wire 24 extending out of the proximal end of the second dilatation catheter is manipulated by hand to prevent its advancement within the vascular system 10 during the distal movement of the second dilatation catheter. The balloon of the second dilatation catheter is then positioned across the stenosis 19, so that upon inflation of that balloon, the stenosis 19 is further dilated. The dilatation catheter exchange procedure has now been completed, and the guide wire captivation catheter 30 can be left in the guide catheter 22 until no further exchanges are necessary (i.e., until the guide wire 24 can be withdrawn from across the stenosis).

During the dilatation catheter removal and installation procedure, the position of the guide wire is maintained relative to the guide catheter and, more importantly, relative to the stenosis, without the previously required task of holding the guide wire by hand from outside of the body. Since the guide wire no longer must be continually manipulated, the previously required extension or exchange wires used to facilitate handling of the guide wire are no longer necessary (i.e. the guide wire can be shorter). Additionally, the procedure may be performed without a second skilled physician, who was previously necessary to continually manipulate the guide wire. Finally, the dangerously prolonged use of x-ray fluoroscopy used to observe the position of the guide wire is no longer necessary since the guide wire is held stationary by use of the present invention and thus its position need not be continuously observed.

Second Embodiment (FIGS. 4 and 5)

Another embodiment of the guide wire captivation catheter of the present invention is shown in FIGS. 4 and 5. A guide catheter 50 provides a partial path through the arterial system for a dilatation catheter 51 having a main inflation lumen shaft 52 and a distal dilatation balloon 53. The dilatation catheter 51 is an over-the-wire catheter, which is movable along a guide wire 54 which is positioned within the guide catheter 50. As is typical, the proximal end of the shaft 52 is mounted to an inflation manifold 55 through which the guide wire extends. A guide catheter manifold 56 is affixed on the proximal end of the guide catheter 50.

In this embodiment, the wire captivation balloon is fixed to the guide catheter. An inflation lumen 62 is formed in the wall of the guide catheter 50, between an inner wall surface 64 and an outer wall surface 66. At a proximal end of the guide catheter 50 an inflation device (not shown) is connected to the inflation lumen 62, either directly or via a coupling 67. An annular inflatable balloon 68 is mounted within the guide catheter 50 adjacent its distal end, and is in fluid communication with the inflation lumen 62. The inflation lumen 62 thus provides a fluid path to the inflatable balloon 68 located adjacent the guide catheter distal end 70. Upon inflation, the inflatable balloon 68 expands to a size that limits longitudinal movement of the guide wire 54 relative to the guide catheter 50.

The method of dilatation catheter exchange incorporating this preferred embodiment of the present invention is very similar to the previously described, improved method of dilatation catheter exchange. However, in this embodiment of the present invention, the inflation lumen 62 and the inflatable balloon 68 are integral with or fixed to the guide catheter 50 so that neither the inflation lumen 62 nor the balloon 68 need be inserted or removed from the guide catheter. The inflatable balloon 68 is used in the same way as in the previous improved method of the dilatation catheter exchange, but is not movable longitudinally relative to the guide catheter.

Of course, other configurations for the guide wire captivation catheter of the present invention are contemplated. For instance, the inflatable balloon 68 can be a shape other than annular—it could extend out from only one side of the inner wall of the guide catheter 50, pushing the guide wire 54 against the opposite side of the inner wall of the guide catheter 50.

In another variation, the inflation lumen 62 may be separate from the guide catheter 50, so that it extends through the lumen of the guide catheter 50, as does the guide wire 54. However, in this configuration, the inflation lumen 62 is connected to an inflatable balloon 68 which is fixed to the guide catheter 50.

Third Embodiment (FIGS. 6–8)

Another embodiment of the present invention, as shown in FIGS. 6–8, employs a guide wire captivation wire 98 positioned within a guide catheter 80. The guide catheter 80 provides a partial path through the arterial system for a dilatation catheter 81 having a main inflation lumen shaft 82 and a distal dilatation balloon 83. The dilatation catheter 81 is an over-the-wire catheter, which is movable along guide wire 84 positioned within the guide catheter 80. As is typical, the proximal end of the shaft 82 is mounted to an inflation manifold 85 through which the guide wire extends. A guide catheter manifold 86 is affixed to the proximal end of the guide wire 80.

In this embodiment, a lumen 90 is formed in a wall of the guide catheter 80, between an inner wall surface 92 and an outer wall surface 94 (see FIG. 8). The lumen 90 has a distal end adjacent the distal end of the guide catheter 80 and a proximal end adjacent the proximal end of the guide catheter 80. The distal end of the guide wire captivation wire 98 is fixed to the distal end of guide catheter 80 at wire receptor 99. The guide wire captivation wire 98 has a looped portion 100 extending out of the lumen 90, positioned just proximal of the distal end of the guide catheter 80.

A spiraled recess 102 is formed within the wall of the guide catheter 80, positioned just proximal of the distal end of guide catheter 80 and aligned to receive the looped portion 100 of the wire-captivation wire 98. The guide wire captivation wire 98 extends out of a distal end 103 of the lumen 90 and forms an open loop within the spiraled recess 102, with its distal end received in and fixed to the guide catheter 80 at wire receptor 99. The looped portion 100 of the captivation wire 98 thus is flush or below the inner wall surface of the guide catheter inside diameter. Thus, the loop portion 100 of wire-captivation wire 98 in its open loop state does not interfere with the movement and functioning of guide wire 84 or dilatation catheter 81 within the guide catheter 80.

A proximal end of the captivation wire 98 is connected to a tab member 104 which is slidably mounted relative to the guide catheter manifold 86 at the proximal end of guide catheter 80. A detent 108 is formed on the proximal end of tab member 104 and forcibly fits within a distal groove 110 or a proximal groove 112 of the guide catheter manifold 86.

The loop portion 100 of wire-captivation wire 98 is capable of being in either an open loop state (FIG. 6) or a closed loop state (FIG. 7). The loop state is changed by the longitudinal movement of tab member 104 relative to the manifold 86. The tab member 104 is connected to the proximal end of the wire-captivation wire 98 such that longitudinal movement of tab member 104 causes longitudinal movement of wire 98, except for its fixed distal end. Pushing the tab member 104 distally relative to the guide catheter pushes the wire-captivation wire distally thereby moving the loop portion 100 to its open loop state. Pulling the tab member 104 proximally relative to the guide catheter pulls the wire-captivation wire 98 proximally, thereby pulling the wire forming the loop portion 100 into the lumen 90 via its distal end 103. This effectively moves the loop portion 100 to its closed loop state. The detent 108 of tab member 104 fits into distal groove 110 and proximal groove 112 such that tab member 104 is selectively retained into one of the two grooves to place the captivation wire 98 in its open loop state and closed loop state, respectively.

FIGS. 6 and 7 show the relative positions of a guide wire and dilatation catheter positioned within the distal end of the guide catheter 80 for a dilatation catheter exchange. The guide wire 84 extends through the open loop portion 100 of captivation wire 98 and the dilatation catheter 81 is moved proximally on the guide wire 84 (which is held in place by hand, outside of the body) until the balloon 83 is positioned proximally of the loop portion 100. Radiopaque markers on the balloon or catheter shaft and on the captivation wire 98 permit relative positioning of the balloon 83 and the loop portion 100. As illustrated in FIG. 6, the guide wire 84 is thus exposed and uncovered distally of balloon 83 and within the loop portion 100 adjacent the distal end of the guide catheter 80.

To fix the position of the guide wire 84 for exchange purposes, the tab member 104 is moved proximally to engage proximal grove 112 thereby shrinking the open loop portion 100 down onto the guide wire 84. The captivation wire 98 is drawn taut, urging the guide wire 84 against the inner wall of the guide catheter 80. In its closed state (as seen in FIG. 7) the captivation wire 98 limits longitudinal movement of the guide wire 84 relative to the guide catheter 80. The loop portion 100 in its closed loop state is reduced to a size such that the guide wire 24 is trapped at the distal end of the guide catheter 80.

The method of dilatation catheter exchange incorporating this third embodiment of the present invention is very similar to the previously-described, improved methods of dilatation catheter exchange.

Once the guide wire 84 has been fixed in place by manipulation of the tab member 104, the dilatation catheter 81 is withdrawn and a second dilatation catheter inserted onto the guide wire 84. Thus, the majority of the exchange procedure is accomplished without the necessity of holding onto the guide wire at a position outside the body and quite remote from the lesion. In this embodiment of the present invention, the loop portion 100 of wire-captivation 98 is fixed within the distal end of guide catheter 80. Thus, as opposed to other variations of the invention, the means for engaging the guide wire need not be inserted or removed from the guide catheter during the exchange procedure. The loop portion 100 of wire-captivation wire 98 is used to trap the guide wire 84 in a similar fashion as the inflatable captivation balloon of the other preferred embodiments. The loop portion 100 of wire 98 closes to trap the guide wire 84 within the guide catheter 80 whereas in the previously described methods, inflation of the captivation balloon effectively trapped the guide wire. Also, the loop portion 100 when opened allows longitudinal movement of the guide wire 84 relative to the guide catheter 80, whereas in the previously described inventive method, the deflated captivation balloon allowed relatively unrestricted longitudinal movement of the guide wire within the guide catheter.

Conclusion

The present invention offers the advantages of allowing pre-angioplasty dilatation catheter selection and guide wire selection, with the ability to later exchange dilatation catheters quickly and without longitudinal guide wire movement in the guide catheter. Another advantage is the ability of one person to perform the dilatation catheter exchange. Previously, more than one person was usually necessary to perform the dilatation catheter exchange, since one person must be available to manipulate the guide wire to hold it in position while the another person exchanges the catheters. Also, the cumbersome, long or extendable exchange wires, which were used to maintain guide wire position, are no longer required to perform a dilatation catheter exchange using the inventive structure and exchange method of the present invention. Finally, the dangerously prolonged use of x-ray fluoroscopy is no longer necessary to continuously observe the movable guide wire position, since the guide wire can now be fixed in position.

Although the present invention has been described with reference to preferred embodiments, workers skilled in the art will recognize that changes may be made in form and detail without departing from the spirit and scope of the invention.

What is claimed is:

1. An angioplasty catheter system, comprising:
 a. a guide wire;
 b. a balloon catheter including an elongated tubular shaft with a balloon connected at a distal end thereof, the shaft including a guide wire lumen receiving the guide wire therethrough;
 c. an elongated tubular guide catheter defining a guide lumen having a proximal end and a distal end and receiving the balloon catheter therethrough;

d. means, nearer the distal end of the guide catheter than the proximal end, for selectively engaging the guide wire to the guide catheter to restrict longitudinal movement of the guide wire relative to the guide catheter, said means for selectively engaging including means for urging a portion of the guide wire against an inner portion of the guide catheter, wherein said means for urging includes a captivation wire extending longitudinally within the guide catheter, the captivation wire having a proximal end, a loop portion, and a distal end, with the distal end being within and adjacent to the distal end of the guide catheter, and the loop portion being just proximal of the distal end of the guide catheter, and wherein the guide wire extends through the loop portion of the captivation wire, with the loop portion having an open loop state whereby unrestricted longitudinal movement of the guide wire through the loop portion and relative to the guide catheter is allowed and a closed loop state whereby longitudinal movement of the guide wire through the loop portion and relative to the guide catheter is limited.

2. The angioplasty catheter system of claim 1 wherein the guide catheter has a spiraled recess formed within an inner wall of the guide catheter to receive the loop portion of the captivation wire in its open loop state.

3. The angioplasty catheter system of claim 1 wherein the guide catheter has a longitudinally extending lumen formed in a wall of the guide catheter for slidable reception of the captivation wire.

4. The angioplasty catheter system of claim 1 wherein the distal end of the captivation wire is fixed within the distal end of the guide catheter.

5. The angioplasty catheter system of claim 1 wherein the means for urging further includes
   means for moving the captivation wire between its open loop state and closed loop state.

6. The angioplasty catheter system of claim 5 wherein the distal end of the captivation wire is affixed to the guide catheter, and wherein the means for moving includes:
   means for pulling the proximal end of the captivation wire in a proximal direction.

7. The angioplasty catheter system of claim 6 wherein the means for moving includes:
   means for holding the captivation wire in its open loop state and in its closed loop state.

8. The angioplasty catheter system of claim 6 wherein the means for pulling includes:
   a tab member mounted to the guide catheter adjacent a proximal end thereof, the tab member having the proximal end of the captivation wire connected thereto, and the tab member being movable longitudinally with respect to the guide catheter between a first distal position whereby the captivation wire is in its open loop state, and a second proximal position whereby the captivation wire is in its closed loop state.

9. The angioplasty catheter system of claim 8 wherein the means for pulling further includes:
   detent means for selectively retaining the tab member in its first distal position or its second proximal position.

10. A method for operating an angioplasty catheter system to limit guide wire movement, the method comprising the steps of:
   a. providing a guide catheter having a first end and a second end with a lumen defined therebetween;
   b. providing a catheter guide wire within the lumen of the guide catheter;
   c. providing an angioplasty balloon catheter within the lumen of the guide catheter slidably disposed relative to the guide wire;
   d. providing means for selectively engaging the guide wire to the guide catheter, said means for selectively engaging including a wire-captivation wire having a loop portion within the guide catheter for receiving the guide wire; and,
   e. manipulating the means for engaging to force the guide wire against an inner portion of the guide catheter.

11. The method of claim 10 wherein the step of manipulating the means for engaging further includes:
   maneuvering the wire-captivation wire to close the loop portion of the wire-captivation wire and thereby force the guide wire against an inner portion of the guide catheter.

12. A method for exchanging a first over-the-wire catheter on a guide wire in a patient's vascular system for a second over-the-wire catheter on the guide wire, wherein the guide wire extends through and past a distal end of a guide catheter, the method comprising the steps of:
   providing a guide wire-captivation wire within the guide catheter;
   holding a proximal end of the guide wire outside of the vascular system to maintain position of the guide wire longitudinally relative to the guide catheter and the vascular system;
   moving the first over-the-wire catheter on the guide wire into the guide catheter to a position proximal of an open portion of the wire-captivation wire; closing the open portion of the wire-captivation wire whereby movement of the guide wire longitudinally relative to the guide catheter is limited;
   releasing the proximal end of the guide wire;
   withdrawing the first over-the-wire catheter from a proximal end of the guide wire;
   installing the second over-the-wire catheter onto the proximal end of the guide wire;
   moving the second over-the-wire catheter to a position just proximal of the closed open portion of the wire-captivation wire;
   holding the proximal end of the guide wire outside of the vascular system to maintain position of the guide wire longitudinally relative to the guide catheter and the vascular system;
   reopening the open portion of the wire-captivation wire to release the guide wire from its fixed position relative to the guide catheter; and
   moving the second over-the-wire catheter distally of the open portion of the wire-captivation wire.

13. The method of claim 12, and further comprising the step of:
   positioning the open portion of the wire-captivation wire within the guide catheter adjacent a distal end of the guide catheter.

14. An angioplasty catheter system, comprising:
   a. a guide wire;
   b. a balloon catheter including an elongated tubular shaft with a balloon connected at a distal end thereof, the shaft including a guide wire lumen receiving the guide wire therethrough;
   c. an elongated tubular guide catheter defining a guide lumen having a proximal end and a distal end and receiving the balloon catheter therethrough;

d. means, nearer the distal end of the guide catheter than the proximal end, for selectively engaging the guide wire to the guide catheter to restrict longitudinal movement of the guide wire relative to the guide catheter, said means for selectively engaging including means for urging a portion of the guide wire against an inner portion of the guide catheter, wherein said means for urging includes an inflatable restriction balloon, within the distal end of the guide lumen, designed to engage the guide wire relative to the guide catheter when inflated, and means, coupled to the inflatable restriction balloon, for inflating the inflatable restriction balloon, the inflation of which restricts longitudinal movement of the guide wire relative to the guide catheter; and, e. said inflatable restriction balloon is carried at a distal end of an elongated tubular flexible shaft, the shaft is adapted for insertion within the guide catheter to position the inflatable restriction balloon proximate to the distal end of the guide catheter and an inflation lumen is defined through said shaft to provide a means for inflating the inflatable restriction balloon.

15. An angioplasty catheter system, comprising:

a. a guide wire;

b. a balloon catheter including an elongated tubular shaft with a balloon connected at a distal end thereof, the shaft including a guide wire lumen receiving the guide wire therethrough;

c. an elongated tubular guide catheter defining a guide lumen having a proximal end and a distal end and receiving the balloon catheter therethrough;

d. means, nearer the distal end of the guide catheter than the proximal end, for selectively engaging the guide wire to the guide catheter to restrict longitudinal movement of the guide wire relative to the guide catheter, said means for selectively engaging including means for urging a portion of the guide wire against an inner portion of the guide catheter, wherein said means for urging includes an inflatable restriction balloon, within the distal end of the guide lumen, designed to engage the guide wire relative to the guide catheter when inflated, and means, coupled to the inflatable restriction balloon, for inflating the inflatable restriction balloon, the inflation of which restricts longitudinal movement of the guide wire relative to the guide catheter; and, e. said means for inflating further including a tube with an inflation lumen which is separate from the guide catheter.

16. The angioplasty catheter system of claim 15 wherein the tube is movable longitudinally with respect to the guide catheter.

17. An angioplasty catheter system, comprising:

a. a guide wire;

b. a balloon catheter including an elongated tubular shaft with a balloon connected at a distal end thereof, the shaft including a guide wire lumen receiving the guide wire therethrough;

c. an elongated tubular guide catheter defining a guide lumen having a proximal end and a distal end and receiving the balloon catheter therethrough;

d. means, nearer the distal end of the guide catheter than the proximal end, for selectively engaging the guide wire to the guide catheter to restrict longitudinal movement of the guide wire relative to the guide catheter, said means for selectively engaging including means for urging a portion of the guide wire against an inner portion of the guide catheter, wherein said means for urging includes an inflatable restriction balloon, within the distal end of the guide lumen, designed to engage the guide wire relative to the guide catheter when inflated, and means, coupled to the inflatable restriction balloon, for inflating the inflatable restriction balloon, the inflation of which restricts longitudinal movement of the guide wire relative to the guide catheter; and, e. said means for urging includes means for carrying the inflatable balloon separate from the guide catheter.

18. The angioplasty catheter system of claim 17 wherein the inflatable balloon is movable longitudinally with respect to the guide catheter.

19. An angioplasty catheter system, comprising:

a guide wire;

an elongated tubular guide catheter defining a guide lumen having a proximal end and a distal end;

a balloon catheter received in the guide lumen of the guide catheter, the balloon catheter including an elongated tubular shaft with a balloon connected at a distal end thereof, the guide wire being slidably disposed through a guide wire lumen defined through said shaft; and a movable captivation catheter which is separate from the guide wire and received in the lumen of the guide catheter, the captivation catheter including an elongated tubular shaft with a captivation balloon connected at a distal end thereof, the captivation balloon designed to selectively engage the guide wire relative to the guide catheter when inflated within the lumen of the guide catheter at a position distal to the distal end of the balloon catheter.

20. A method for operating an angioplasty catheter system to limit guide wire movement, the method comprising the steps of:

providing a guide catheter having a proximal end and a distal end with a lumen defined therebetween;

providing a catheter guide wire within the lumen of the guide catheter;

providing an angioplasty balloon catheter within the lumen of the guide catheter slidably disposed relative to the guide wire, the balloon catheter having a proximal end and a distal end;

providing a movable captivation catheter within the lumen of the guide catheter, which includes an elongated tubular shaft with a captivation balloon connected at a distal end thereof;

advancing the captivation catheter through the lumen of the guide catheter until the captivation balloon is positioned distal to the distal end of the balloon catheter and proximal to the distal end of the guide catheter; and inflating the captivation balloon to force the guide wire against an inner wall of the lumen in the guide catheter.

* * * * *